US008125523B2

(12) United States Patent
Zhang et al.

(10) Patent No.: US 8,125,523 B2
(45) Date of Patent: Feb. 28, 2012

(54) DEVICE AND METHOD FOR ULTRASONIC VIDEO DISPLAY

(75) Inventors: Xuewu Zhang, Shenzhen (CN); Song Chen, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 797 days.

(21) Appl. No.: 12/257,255

(22) Filed: Oct. 23, 2008

(65) Prior Publication Data

US 2009/0268087 A1 Oct. 29, 2009

(30) Foreign Application Priority Data

Apr. 29, 2008 (CN) .......................... 2008 1 0067021

(51) Int. Cl.
*H04N 5/66* (2006.01)
*H04N 7/01* (2006.01)
(52) U.S. Cl. ........ 348/163; 348/166; 348/441; 348/444; 348/453; 348/739
(58) Field of Classification Search .......... 348/163–166, 348/441–445, 453, 455–456, 739
See application file for complete search history.

(56) References Cited

U.S. PATENT DOCUMENTS

| | | | |
|---|---|---|---|
| 5,790,111 A * | 8/1998 | Wood et al. ................... 345/213 |
| 6,226,040 B1 * | 5/2001 | Kuo et al. ...................... 348/441 |
| 6,508,763 B1 | 1/2003 | Urbano et al. | |
| 2002/0085116 A1 * | 7/2002 | Kuwano et al. ............... 348/465 |
| 2004/0183945 A1 * | 9/2004 | Ochiai et al. .................. 348/441 |
| 2008/0170159 A1 * | 7/2008 | Akiyama et al. .............. 348/739 |
| 2008/0313377 A1 * | 12/2008 | Kawano et al. ............... 710/244 |

FOREIGN PATENT DOCUMENTS

CN  200969622 Y  10/2007

OTHER PUBLICATIONS

Sheng Lei et al., "Design and realization of real-time video-processing platform based on DSP and FPGA," Journal of University of Science and Technology of China, vol. 36, No. 3, Mar. 2006, pp. 304-309.
Li Gang et al., "A real-time video processing system based on FPGA and DSP," Computer Simulation, 2005 22(10).

* cited by examiner

*Primary Examiner* — Bharat Barot
(74) *Attorney, Agent, or Firm* — Kory D. Christtensen; Stoel Rives LLP

(57) ABSTRACT

An ultrasonic video display device may comprise a memory; a programmable logic device, which may comprise a VGA signal receiving module for receiving and demodulating digital video signals and a video signal processing module including a memory controller, a gamma correcting unit, a scaling processing unit, a filtering unit, a chrominance space converting unit, a chrominance sampling unit and an interleaved sampling controller. The ultrasonic video display may also include a first digital-to-analog converter having an input coupled to an output of the VGA signal receiving module to convert the digital video signals into VGA analog signals and to output the VGA analog signals. A second digital-to-analog converter may receive video digital signals, convert the video digital signals into video analog signals, and output the video analog signals.

8 Claims, 3 Drawing Sheets

DEVICE AND METHOD FOR ULTRASONIC VIDEO DISPLAY

RELATED APPLICATIONS

This application claims priority to Chinese Patent Application No. 200810067021.X, filed Apr. 29, 2008, for "DEVICE AND METHOD FOR ULTRASONIC VIDEO DISPLAY," the disclosure of which is fully incorporated herein by reference.

TECHNICAL FIELD

This disclosure relates to ultrasonic imaging devices, and particularly to a display device of an ultrasonic imaging apparatus and a method thereof.

BRIEF SUMMARY

An ultrasonic video display device and method for ultrasonic video display are disclosed.

DETAILED DESCRIPTION OF PREFERRED EMBODIMENTS

A display section of typical medical ultrasonic imaging apparatus usually adopts two (2) display types, e.g., a Video Graphics Array (VGA) display and a Video display. The resolution of the VGA display is sometimes as high as 1280×1024 pixels, or even higher; while a Video display system may support analog television signals, (e.g., Phase Alternating Line (PAL), National Television System Committee (NTSC), Sequential Color with Memory (SECAM), and the like), video printing, video storage, and the like.

In a typical display system, a VGA digital video signal received from a computing device, such as a personal computer (PC), is sent to a programmable logic device (e.g., a Field Programmable Gate Array (FPGA), a Complex Programmable Logic Device (CPLD), an Application Specific Integrated Circuit (ASIC), or the like), where the signal may be buffered and output to a video encoder, while the signal is simultaneously output for display. The programmable logic device outputs the final Video (analog video).

Figure 1:
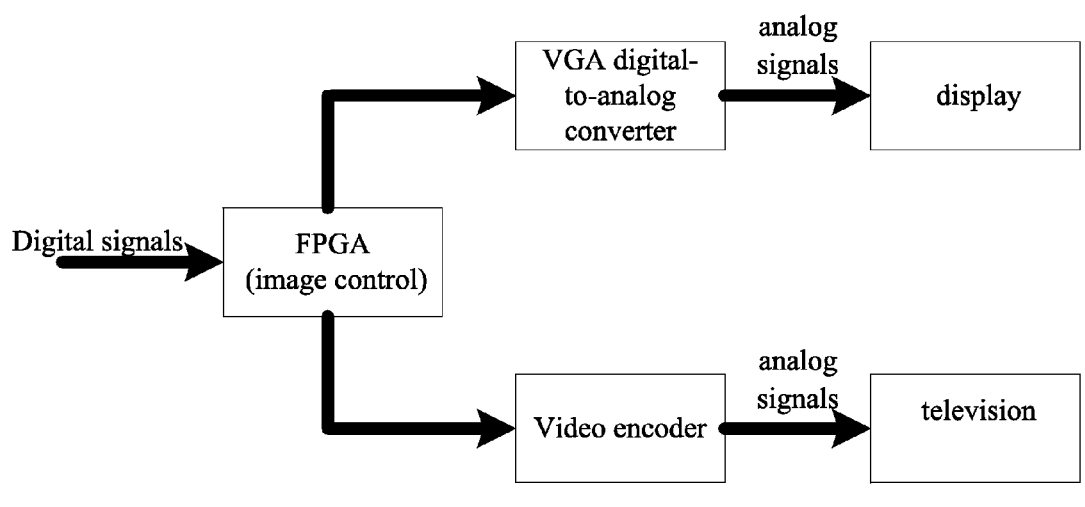
FIG. 1 is a schematic block diagram of an existing display processing system.

The flow of such a display processing system is depicted in FIG. 1. In a medical ultrasonic imaging apparatus, VGA and Video are output at the same time. However, the resolution of VGA is relatively higher than that of Video, which is 720×576 for PAL and 720×480 for NTSC. Furthermore, data formats for VGA and Video are different. A VGA digital signal is usually in RGB format (8:8:8), while a television signal is usually in YCbCr (4:2:2) format. As such, special video chip processes are required to output a video display signal, and the image quality of the output signal is poor.

Typical ultrasonic display areas are 800×600 or 640×480, so that VGA signals and Video signals on the display area can be displayed at the same time. However, in order to display VGA signals with a high resolution under a Video format, the signal is typically stored into a picture file and then displayed after post processing. Only analog video signals can be output, and the extendibility and versatility thereof are very poor, even though some signals with a low resolution (such as 1024×768, 800×600, or less) can be processed by special chips. In the case of a traditional display system, the operations of a programmable logic device receive VGA signals from a PC and buffer and output them without any processing. Therefore, the programmable logic device is only used to control an external video encoder, and the quality of the output images depends on the functionality and/or performance of the external video encoder. The external video encoder performs three stages of processing, including pre-processing, practical video coding and decoding, and video post-processing. In addition, the external video encoder may also provide the supported video standards, algorithms, and video structures. Some encoders may provide poor video output performance and/or inadequate flexibility because of limited video signal processing algorithms, requirements for sizes of input and output video images. This may preclude displaying the same picture in real time by means of Video and VGA, displaying VGA signals with a high resolution (e.g., 1280×1024) in real time, and/or displaying VGA images in any area as needed by a user.

The device and method disclosed herein may provide a video display capable of processing input signals in various standard resolutions and/or simultaneously display the same pictures through VGA signals and various Video signals.

In some embodiments, an ultrasonic video display device according to this disclosure may comprise a memory to buffer for video data; a programmable logic device comprising a VGA signal receiving module for receiving and demodulating digital video signals; and a video signal processing module including a memory controller, a gamma correcting unit, a scaling processing unit, a filtering unit, a chrominance space converting unit, a chrominance sampling unit and an interleaved sampling controller. The VGA signal receiving module may demodulate digital video signals and output the demodulated digital video signals to a memory controller. The memory controller may detect frame start information in the digital video signals and, upon detecting the frame start information, store the video signals into a memory on a frame-by-frame basis. The memory may read out the digital video signals every other frame, and send the same to the video signal processing module. The video signal processing module may perform various video processes, including, but not limited to: gamma correction, scaling processing, two-dimensional filtering, chrominance space converting, double sampling of chrominance, and interleaved sampling processing for the digital video signals in sequence, and the like. The video signal processing module may then output one or more processed digital video signals.

A first digital-to-analog converter may receive the output of the VGA signal receiving module to convert and output the digital video signals therefrom as VGA analog signals. A second digital-to-analog converter for may receive Video digital signals and covert the received signals into Video analog signals.

A method to provide an ultrasonic video display according to the teachings of this disclosure may include receiving and demodulating digital video signals by a VGA signal receiving module. The method may also include outputting the demodulated digital video signals to a first digital-to-analog converter and a memory controller at the same time, wherein the first digital-to-analog converter converts the digital video signals into VGA analog signals and outputs the VGA analog signals, and the memory controller detects the frame start information of the digital video signals and, upon detecting the frame start information, stores the video signals into a memory on a frame-by-frame basis reading out the stored digital video signals every other frame from the memory and sending the same to a video signal processing module, which may perform gamma correction, scaling processing, two-dimensional filtering, chrominance space converting, double sampling of chrominance and interleaved sampling processing on the digital video signals in sequence and output Video digital signals to a second digital-to-analog converter.

The method may also include converting the Video digital signals into Video analog signals and outputting the converted Video analog signals.

In another embodiment, the method may include, after the gamma correction and before the filtering of the digital video signals, receiving a user selection of input resolutions and performing video scaling processing for the digital video signals according to the user selection (e.g., by the video scaling unit).

The method may further include, after interleaved sampling the digital video signals, receiving a user selection of output modes and performing video format converting processing for the digital video signals according to the user selection (e.g., by the video format converting unit).

In another embodiment, the method according to the teachings of this disclosure may comprise, after the gamma correction and before the video scaling processing of the digital video signals, receiving a user selection of a display area and performing display area processing for the digital video signals according to the user selection (e.g., by the display area control unit).

Figure 2:
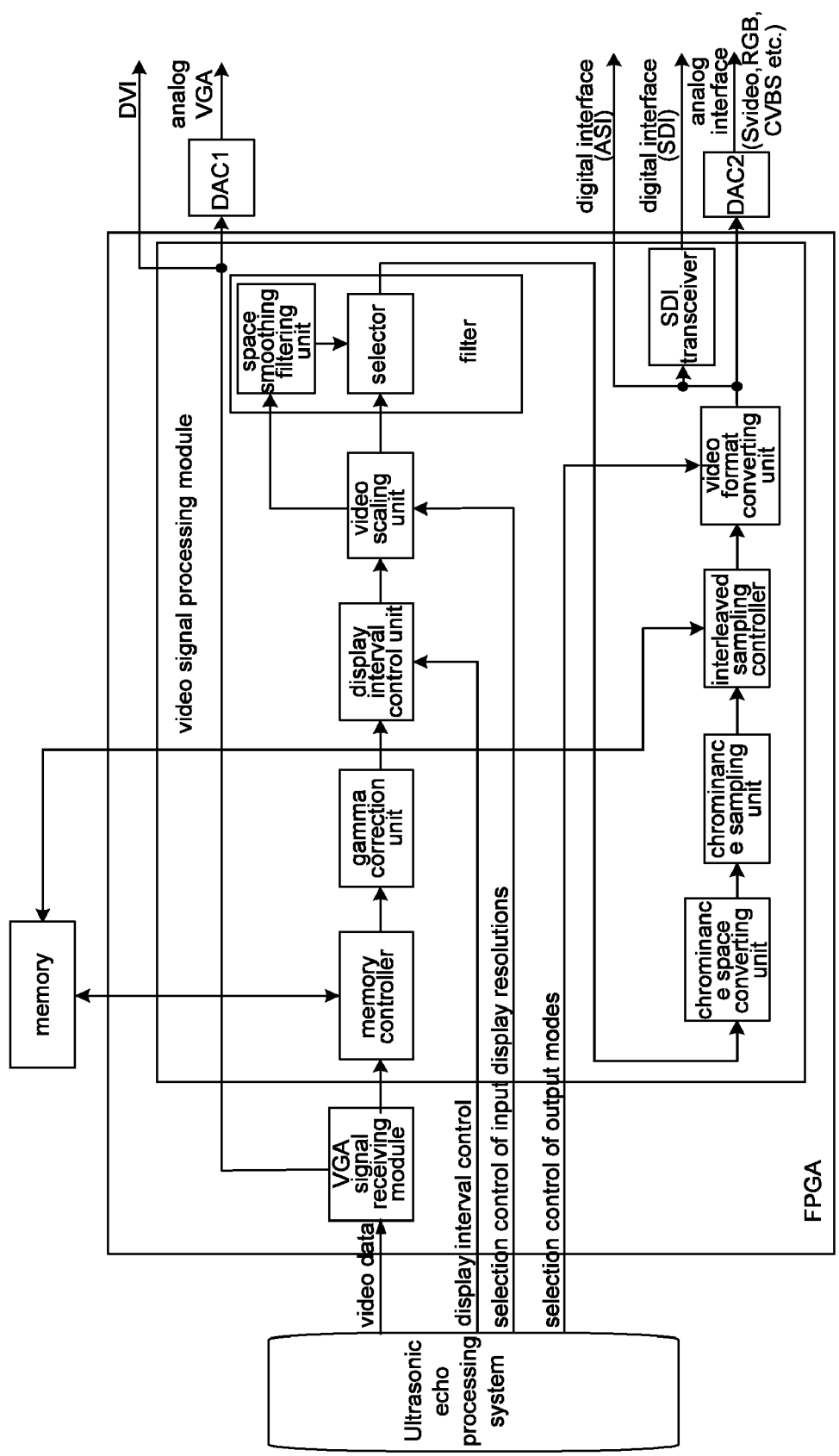
FIG. 2 is a schematic block diagram of an ultrasonic video display device.

FIG. 2 shows one embodiment of an ultrasonic video display device. The display device of FIG. 2 may comprise a memory, a logic device, a first digital-to-analog converter DAC1, and a second digital-to-analog converter DAC2.

The programmable logic device may be a FPGA or any other type of programmable logic device known in the art (e.g., a CPLD, ASIC, or the like). Accordingly, although FIG. 2 shows the programmable logic device as an FPGA, one skilled in the art would recognize that any programmable logic device could be used in its place.

The programmable logic device may receive and demodulate digital video signals, perform video signal processing, and/or control storage operations of a memory. The programmable logic device may further comprise a VGA signal receiving module for receiving and demodulating digital video signals, and a video signal processing module, which may comprise a memory controller, a gamma correcting unit, a scaling processing unit, a filtering unit, a chrominance space converting unit, a chrominance sampling unit, and an interleaved sampling controller.

The memory may function as a buffer for video data and converted (processed) video data. The memory may be any memory storage media known in the art including, but not limited to: an SSRAM, an SDRAM, a DDR RAM, or the like.

The first digital-to-analog converter DAC1 may function as a channel for VGA data to be converted into analog data and output. The DAC1 may receive digital video signals from the VGA signal receiving module and convert them into VGA analog signals. The DAC1 may output the converted VGA analog signals. A second digital-to-analog converter DAC2 may function as a channel for Video (digital video) data to be converted into analog data and output. The DAC2 may receive buffered and processed digital video signals. The DAC2 may convert the digital video signals into Video analog signals and output the Video analog signals.

The VGA signal receiving module may receive digital video signals comprising ultrasonic digital VGA image signals and/or digital video image signals (e.g., in VGA, LVDS format or the like) from a SDVO interface of a computing device (such as an ultrasonic echo processing system, a PC, or the like). The VGA signal receiving module may demodulate the digital video signals and split them into two (2) signals, which may be output to the first digital-to-analog converter DAC1 and to the memory controller, respectively.

The first digital-to-analog converter DAC1 may convert the digital video signals into VGA analog signals and output the VGA analog signals. Alternatively, or in addition, the digital video signals may be directly output in DVI format without being processed by the first digital-to-analog converter DAC1.

After receiving the demodulated digital video signals, the memory controller may detect frame start information in the video signals. Upon detecting frame start information, the memory controller may store the video signals in the memory on a frame-by-frame basis. The memory may read out the video signals every other frame and send the same to the video signal processing module. The video signal processing module may perform processing thereon including, but not limited to: gamma correction, scaling processing, two-dimensional filtering, chrominance space converting, double sampling of chrominance and interleaved sampling for the digital video signals in sequence, and output Video digital signals which to the second digital-to-analog converter DAC2. The second digital-to-analog converter DAC2 may convert the Video digital signals and outputs signals in a format, such as S-Video, RGB, CVBS, or the like.

By using the powerful functions of the programmable logic device (e.g., the FPGA of FIG. 2), the digital video signals may be demodulated and split into two (2) parts, one of which may be digital-to-analog converted into VGA analog signals and output to a display, and the other may be converted into Video digital signals (after being read out every other frame and interleaved sampled). The Video digital signals may then be digital-to-analog converted into Video analog signals and output to a display, such as a television, thereby realizing a real-time display of VGA signals and Video signals for digital video signals of various resolutions.

In some embodiments, the programmable logic device may provide additional functions, such as video format conversion, display area control, and the like. In addition, the programmable logic device may output corresponding digital video signals according to a user's selection, and perform video display in the image areas selected by the user.

In some embodiments, the video signal processing module may further comprise a video scaling unit and a video format converting unit. The video scaling unit may be connected to the gamma correcting unit and to the filtering unit, and may be used to receive and process a user selection of input resolutions. The video format conversion unit may be connected to the interleaved sampling controller and the to second digital-to-analog converter DAC2. The video format conversion unit may be used to receive and process a user selection output modes, so that a user can select among various output formats, such as S-VIDEO, RGB, CVBS or the like output by the second digital-to-analog converter DAC2.

In some embodiments, the video signal processing module may further comprise a display area control unit connected to the gamma correcting unit and to the video scaling unit. The display area control unit may be used to receive and process a user selection of a display area.

The programmable logic device may provide various user interfaces by which a user may control the operation of the system, including, but not limited to: selection of image areas, selection of output image formats and image scaling sizes, and selection of image areas with corresponding sizes and video images in corresponding formats, and the like.

In some embodiments, the ultrasonic video display device may output a signal in an additional format by, for example, leading out a signal line from the output side of the video format converting unit and connecting the signal line to an ASI digital interface to output signals in an ASI format. Alternatively, or in addition, a SDI transceiver may be connected at the output side of the video format converting unit to convert the digital video signals into signals in a SDI format for output it to a SDI digital interface. Alternatively, or in addition, a signal line may be provided from the output side of the VGA signal receiving module. This signal line may be connected to a DVI interface to output signals in a DVI format.

Figure 3:
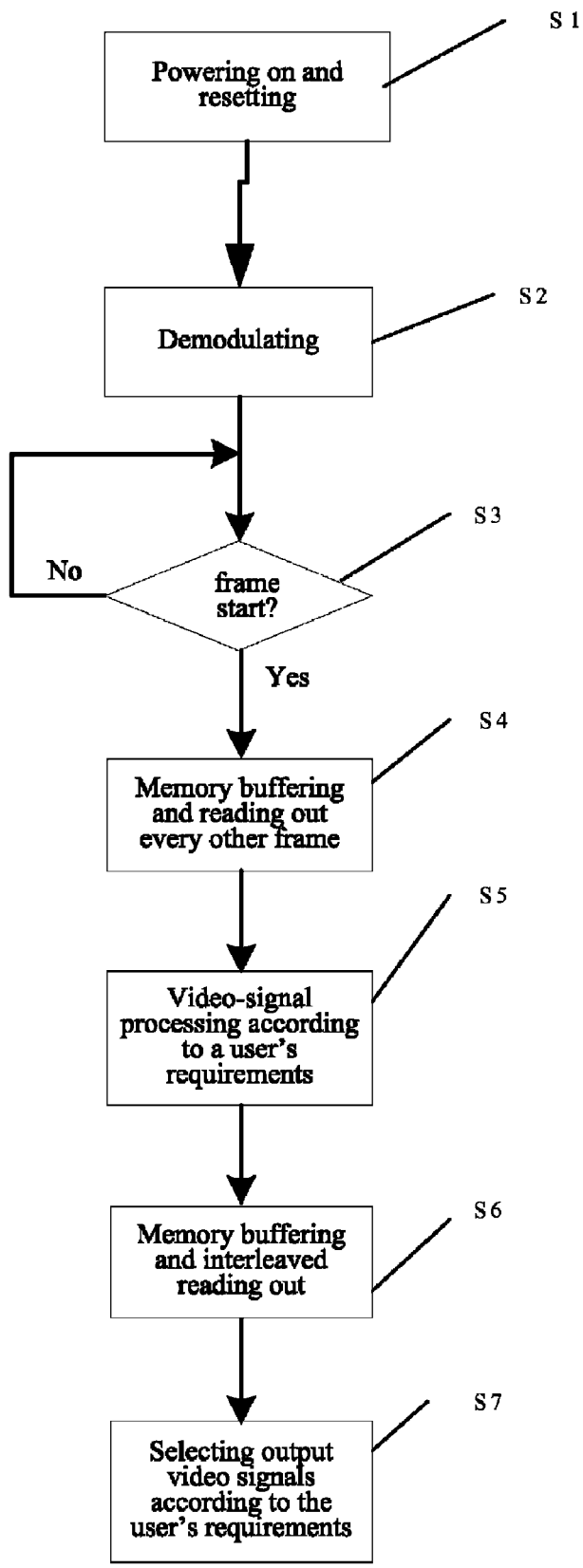
FIG. 3 is a flow diagram of one embodiment of a method for providing a ultrasonic video display.

FIG. 3 is a flow diagram of one embodiment of a method for providing an ultrasonic video display. In step S1, a programmable logic device (such as the programmable logic device described above in conjunction with FIG. 2) may be powered on and reset. The resetting of step S1 may comprise configuring a programmable logic controller, which may comprise loading an FPGA configuration file into an FPGA.

In step S2, an SDVO video signal may be received and demodulated (e.g., by a VGA signal receiving module). The demodulated signals may be converted into an analog VGA signal. As discussed above the conversion of step S2 may be performed by a first digital-analog converter DAC1, which may output VGA analog signals after digital-to-analog conversion. Meanwhile, in step S2, the demodulated signals produced may be made available for frame capture (e.g., by a memory controller, as discussed above in conjunction with FIG. 2).

In step S3, a video signal may be received and start frame information therein may be detected (e.g., by a memory controller or the like). Upon detection of start frame information, the video signal may be stored on a frame-by-frame basis in a memory or other data storage means (e.g., disc, optical media, or the like).

In step S4, the stored video frame information may be obtained and made available for video signal processing. In some embodiments, this may comprise reading every other frame from a data storage means (e.g., memory) and sending the same to a video signal processing module.

In step S5, the video signal may be processed (e.g., by a video signal processing module) according to user selections (e.g., display areas, input resolutions, output image sizes, and the like), which may include, but is not limited to: gamma correction, scaling processing, two-dimensional filtering, chrominance space conversion, double sampling of chrominance (from YUV 4:4:4 to YUV 4:2:2), and the like.

In step S6, the video-signal processed data may be stored in a data storage means (e.g., memory) on a frame-by-frame basis, and interleaved sampled (e.g., by a interleaved sampling controller). The interleaved data may be output for video format conversion (e.g., by a video format conversion unit). The formatted video may be output by a transceiver in a standard format (e.g., output by an SDI transceiver in a standard CCIR656 format).

In step S7, an output and/or corresponding video format may be selected according to a user's requirements. Upon receiving the selection, the SDVO signals may be received from a computer (e.g., by a programmable logic device, such as the FPGA programmable logic device shown in FIG. 2). The signals may be processed for conversion into different formats (e.g., different video standards). For example, VGA signals with high resolutions and various types of Video signals can be displayed in real-time, various types of digital video signals may be output, video display may be provided according to the image areas selected by the user, and the displayed images may be of high quality.

The programmable logic device of this disclosure may provide a high degree of flexibility, support a wide array of image sizes (resolutions) and/or output-formats, and may allow for the use of different types of user interfaces. Users may select images having different sizes and/or cut out images in different areas. Images may be scaled to a desired size and/or output directly. Video may be displayed and/or recorded while securing the availability and fidelity of images.

Although the device and method disclosed herein is discussed in the context of implementations of analog and digital video outputs in medical imaging apparatuses (e.g., ultrasonic devices), this disclosure should be read as limited to such applications. For example, the teachings of this disclosure are also applicable to analog and digital video outputs in PC-based imaging apparatuses in various other fields.

Detailed descriptions of several example embodiments are provided above. However, the invention is not restricted to these example embodiments. Without departing from the scope of the invention, those skilled in this art may make changes and modifications, which will all fall into the claims of the invention.

Furthermore, the described features, operations, or characteristics may be combined in any suitable manner in one or more embodiments. It will also be readily understood that the order of the steps or actions of the methods described in connection with the embodiments disclosed may be changed as would be apparent to those skilled in the art. Thus, any order in the drawings or Detailed Description is for illustrative purposes only and is not meant to imply a required order, unless specified to require an order.

Embodiments may include various steps, which may be embodied in machine-executable instructions to be executed by a general-purpose or special-purpose computer (or other electronic device). Alternatively, the steps may be performed by hardware components that include specific logic for performing the steps or by a combination of hardware, software, and/or firmware.

Embodiments may also be provided as a computer program product including a machine-readable medium having stored thereon instructions that may be used to program a computer (or other electronic device) to perform processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/machine-readable medium suitable for storing electronic instructions.

As used herein, a software module or component may include any type of computer instruction or computer executable code located within a memory device and/or transmitted as electronic signals over a system bus or wired or wireless network. A software module may, for instance, comprise one or more physical or logical blocks of computer instructions, which may be organized as a routine, program, object, component, data structure, etc., that performs one or more tasks or implements particular abstract data types.

In certain embodiments, a particular software module may comprise disparate instructions stored in different locations of a memory device, which together implement the described functionality of the module. Indeed, a module may comprise a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

What is claimed is:

1. An ultrasonic video display device, comprising:
a memory to buffer video data;
a programmable logic device comprising;
a Video Graphics Array (VGA) signal receiving module to receive digital video signals, and
a video signal processing module comprising a memory controller, a gamma correcting unit, a scaling processing unit, a filtering unit, a chrominance space converting unit, a chrominance sampling unit, and an interleaved sampling controller,
wherein the VGA signal receiving module is to demodulate the received digital video signals and to output the demodulated digital video signals to the memory controller, wherein the memory controller is to detect frame start information in the digital video signals and, upon detecting frame start information, to store the video signals in the memory on a frame-by-frame basis, wherein the memory is to read out every other frame of the stored digital video signals and to send the same to the video signal processing module, and wherein the video signal processing module performs gamma correction, scaling processing, two-dimensional filtering, chrominance space converting, double sampling of chrominance and interleaved sampling processing on the digital video signals and outputs video digital signals;
a first digital-to-analog converter coupled to the VGA signal receiving module to convert and output the digital video signals as VGA analog signals; and
a second digital-to-analog converter to convert and output the video digital signals as video analog signals.

2. The ultrasonic video display device according to claim 1, wherein the video signal processing module further comprises:
a video scaling unit; and
a video format converting unit,
wherein the video scaling unit is connected to the gamma correcting unit and to the filtering unit and is to receive and processes a user selection of input resolutions, and wherein the video format converting unit is connected to the interleaved sampling controller and to the second digital-to-analog converter and is to receive and processes a user selection of output formats.

3. The ultrasonic video display device according to claim 2, wherein the video signal processing module further comprises a display area control unit connected to the gamma correcting unit and to the video scaling unit, and wherein the display area control unit is to receive and process a user selection of display areas.

4. The ultrasonic video display device according to claim 3, further comprising a Digital Visual Interface (DVI), interface, a Serial Digital Interface (SDI) transceiver, a SDI interface, and an Asynchronous Serial Interface (ASI) interface,
wherein an input of the DVI interface is coupled to an output of the VGA signal receiving module, an input of the SDI transceiver is coupled to an output of the video format converting unit, an output of the SDI transceiver is coupled to an input of the SDI interface, and an input of the ASI interface is coupled to an output of the video format converting unit.

5. The ultrasonic video display device according to claim 1, wherein the programmable logic device is a field programmable gate array.

6. A method performed by an ultrasonic video display device including a Video Graphics Array (VGA) signal receiving module, a first digital-to-analog converter (DAC), a second DAC, a memory, a memory controller, and a video signal processing module, the method comprising:
receiving and demodulating digital video signals using the VGA signal receiving module;
outputting the demodulated digital video signals to the DAC and the memory controller at the same time, wherein the first digital-to-analog converter converts and outputs the digital video signals as VGA analog signals, and wherein the memory controller detects frame start information in the digital video signals and, upon detecting frame start information, stores the video signals into a memory on a frame-by-frame basis;
reading out every other frame of the digital video signals from the memory and sending the same to the video signal processing module;
performing, using the video signal processing module, one or more of gamma correction, scaling processing, two-dimensional filtering, chrominance space converting, double sampling of chrominance and interleaved sampling processing on the digital video signals; and
converting, using the second DAC, the video digital signals into video analog signals and outputting the video analog signals.

7. The ultrasonic video display method according to claim 6, further comprising:
after the gamma correction and before the filtering of the digital video signals, receiving a user selection of input resolutions and performing video scaling processing on the digital video signals according to the user selection of input resolutions; and
after interleaved sampling the digital video signals, receiving a user selection of output formats and performing video format converting processing for the digital video signals according to the user selection of output formats.

8. The ultrasonic video display method according to claim 7, further comprising:
after the gamma correction and before the video scaling processing of the digital video signals, receiving a user selection of display areas and performing display area processing on the digital video signals according to the user selection of display areas.

* * * * *